United States Patent [19]

Lindberg et al.

[11] Patent Number: 4,469,707
[45] Date of Patent: Sep. 4, 1984

[54] METHOD FOR TREATMENT OF SENILE DEMENTIA

[75] Inventors: Ulf H. A. Lindberg, Södertälje; Sven-Ove Ögren, Nykvarn, both of Sweden

[73] Assignee: Astra Läkemadel Aktiebolag, Södertälje, Sweden

[21] Appl. No.: 500,337

[22] Filed: Jun. 2, 1983

[30] Foreign Application Priority Data

Apr. 29, 1983 [SE] Sweden .................................. 8302452

[51] Int. Cl.³ .......................................... A61K 31/135
[52] U.S. Cl. .................................................... 424/330
[58] Field of Search ........................................ 424/330

[56] References Cited

U.S. PATENT DOCUMENTS 4,237,311 12/1980 Lindberg et al. ................... 560/173
4,331,684 5/1982 Lindberg et al. ................... 424/311

OTHER PUBLICATIONS

Carlsson, A. et al., Adv. Biochem. Psychopharmacol., 23, (1980), pp. 295–304.

Primary Examiner—Stanley J. Friedman
Attorney, Agent, or Firm—Brumbaugh, Graves, Donohue & Raymond

[57] ABSTRACT

A method for treatment of senile dementia comprising administration to a patient of a therapeutically effective amount of a compound of the formula

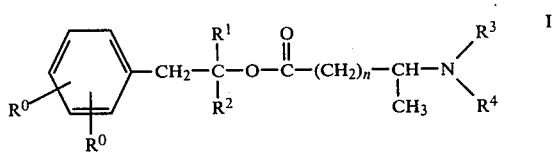

and pharmaceutically acceptable salts thereof, in which formula the groups $R^0$ are the same or different and are selected from the group consisting of hydrogen, halogen, alkyl having 1, 2 or 3 carbon atoms, and alkoxy having 1, 2 or 3 carbon atoms; $R^1$ is hydrogen, methyl or ethyl; $R^2$ is methyl or ethyl; $R^3$ and $R^4$ are the same or different and are hydrogen or an alkyl group having 1, 2 or 3 carbon atoms; and n is 0, 1 or 2.

2 Claims, No Drawings

METHOD FOR TREATMENT OF SENILE DEMENTIA

This invention refers to a method for treatment of dementia, especially senile dementia of the Alzheimer type.

Senile dementia of nonvascular origin, often referred to as Alzheimer's disease, is a common neurological disorder bringing about a loss of intellectual function. It is believed that at least some of the anatomical alterations of dementia in the brain reflects an acceleration of the normal ageing process, but that there are also other factors involved.

Different types of substances have been administered as presumptive drugs in the past in order to prevent or at least alleviate the symptoms of dementia. As examples can be mentioned vasodilators, anticoagulantia, central stimulants, neurotransmitters and neurotransmitter precursors. So far, however, no effective treatment has been found.

In a report on biochemical changes in Alzheimer's disease, Davies P., Res. Publ. Assoc. Res. Nerv. Ment. Dis. 57 (1979), p 153-166, the neurotransmitter and enzyme concentrations in the brain from cases of senile dementia have been investigated. It is concluded that there is clear evidence for an extensive reduction in the activities of the two enzymes, choline acetyltransferase and acetylcholinesterase, being associated with the cholinergic neurotransmission.

In Carlsson A. et al, Adv. Biochem. Psychopharmacol. 23 (1980), p 295-304 an investigation comparing several transmitters in human brain regions from senile dementia cases and controls is described. Generally, low transmitter levels were observed in the dementia cases. In particular low levels of 5-hydroxytryptamine (5-HT) were found in hippocampus, the region of the brain which is believed to be responsible for the memory function.

It has now been clinically shown that certain aralkyl esters of amino acids of the general formula

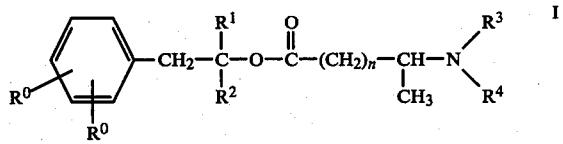

and pharmaceutically acceptable salts thereof, in which formula the groups $R^0$ are the same or different and are selected from the group consisting of hydrogen, halogen, alkyl having 1, 2 or 3 carbon atoms, and alkoxy having 1, 2 or 3 carbon atoms; $R^1$ is hydrogen, methyl or ethyl; $R^2$ is methyl or ethyl; $R^3$ and $R^4$ are the same or different and are hydrogen or an alkyl group having 1, 2 and 3 carbon atoms; and n is 0, 1 or 2, when administered to a patient suffering from senile dementia bring about a considerable reduction of the symptoms thereof.

The aralkyl esters of the formula I are described in US-A-4,237,311. These compounds are known to selectively inhibit the central neuronal uptake of 5-HT and have also been shown not to have an anticholinergic effect, Lindberg U. et al, Journal of Med. Chem. 21 (1978) No. 5, p 448-456.

The compounds of the formula I have now in addition been shown to display a regional specificity in blocking the 5-HT uptake in vivo. The compounds were most potent in the hypothalamus and hippocampus regions of the brain. This nonpredictable regional effect thus indicated a therapeutical potential and suggested clinical trials for the treatment of senile dementia, in which, as mentioned above, there is evidence for a deranged 5-HT function, particularly in the limbic regions.

It has also in animal studies, surprisingly, become apparent that the compounds of the formula I affect the cholinergic system and potentiate the cholinergic response.

The compounds of the invention, thus, have the capability to enhance neurotransmission in the cholinergic as well as the serotoninergic systems in the brain. As mentioned in the introduction deficiencies in both these systems have been demonstrated to occur in senile dementia.

The object of the invention is thus a method for treatment of senile dementia which comprises administration to a patient of a therapeutically effective amount of a compound of the formula I above.

A further object of the invention is a method for treatment of senile dementia which comprises administration of a compound of the formula I in combination with compounds, which physiologically have an agonistic effect on 5-HT and the cholinergic transmission respectively, such as tryptophan, 5-hydroxytryptophan and choline.

Since the compounds of the formula I to be administered in the method of the invention contain at least one asymmetric carbon atom, they exist in the form of optically active forms, and can be resolved into their optical antipodes by well known methods such as by using optically active acids such as tartaric acid, camphor-10-sulphonic acid, dibenzoyl tartaric acid, and the like.

A preferred subgroup of compounds is obtained when, in the formula I above, the groups $R^0$ are the same or different and are selected from halogen alkyl with 1-3 carbon atoms and alkoxy with 1-3 carbon atoms, preferably selected from halogen and methyl. Further another preferred subgroup of compounds is obtained when, in the formula I above, $R^1$ and $R^2$ are methyl and n is 0, or $R^1$ and $R^2$ are methyl, n is 0 and $R^3$ and $R^4$ are hydrogen.

A particularly preferred subgroup of compounds is obtained when, in the formula I above, the groups $R^0$ are selected from halogen, methyl and hydrogen; the groups $R^1$ and $R^2$ are methyl; n is 0; and the groups $R^3$ and $R^4$ are the same or different and are selected from hydrogen and an alkyl group having 1, 2 or 3 carbon atoms. Preferred subgroups within this group are obtained when not more than one of the groups $R^0$ is hydrogen, or when $R^3$ and $R^4$ are hydrogen or when, simultaneously, not more than one of the groups $R^0$ is hydrogen and $R^3$ and $R^4$ are hydrogen.

The compounds of the following formulas can be mentioned as examples of compounds to be used in the method of the invention:

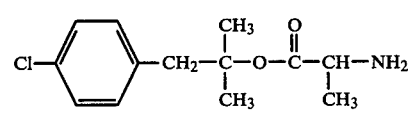

(GEA 654)

-continued

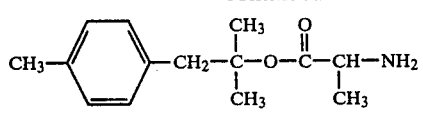 (GEA 937)

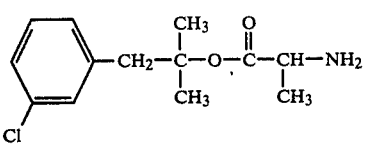 (GEA 935)

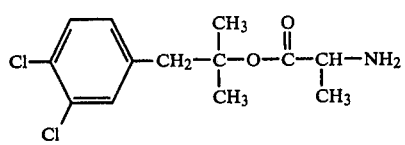 (GEA 699)

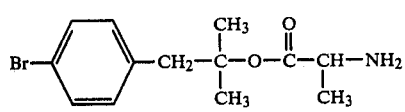 (GEA 917)

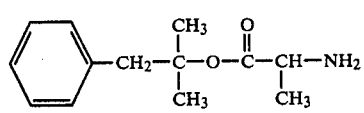 (GEA 916)

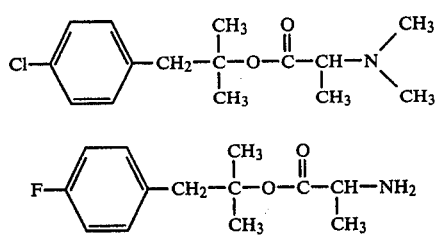 (GEA 953)

(GEA 822)

The compounds of formula I may be prepared by (a) reacting a compound of the formula

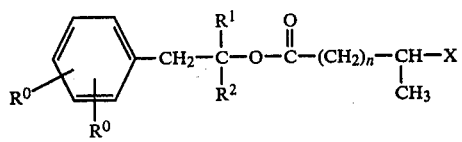 (II)

with an amine of the formula

 (III)

in which formulas $R^0$, $R^1$, $R^2$, $R^3$, $R^4$ and n are defined as above and X is halogen (such as chlorine, bromine or iodine) or p-toluene-sulphonyloxy; or
(b) reacting an alcohol of the formula

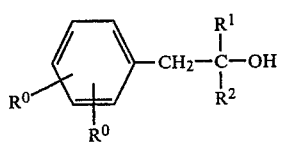 (IV)

with an amino acid, or derivative thereof, of the formula

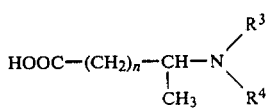 V)

or with an amino acid derivative of the formula

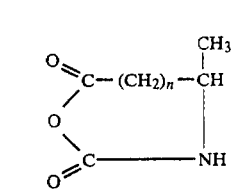 VI)

in which formulas $R^0$, $R^2$, $R^3$, $R^4$ and n are defined as above.

The method (a) above is the preferred method for the preparation of the compounds of the formula I.

The reactions according to both method (a) and (b) are preferably conducted in an inert organic solvent capable of dissolving the reactants. Any suitable pressure and reaction temperature can be used. Preferably, the reactions are carried out under atmospheric or superatmospheric pressure, at a temperature of between $-10°$ and $+100°$ C., preferably between $0°$ and $30°$.

The reaction according to method (b) is preferably conducted in the presence of dry hydrogen chloride as a catalyst. The starting materials of this reaction, i.e. the compounds of the formulas IV and V or VI are known and can be prepared according to methods known per se. For example, the compound of the formula VI can be prepared by reacting phosgene with the appropriate amino acid, optionally an optically active amino acid when an optically active modification of the end product of the formula I is desired.

The compounds of the formula I may be used therapeutically as the racemic mixtures of (+)- and (−)-forms, which in the usual case are obtained at the synthesis. They may also be resolved by methods known per se into the corresponding optically active modifications which, likewise, may be used in therapy. If desired, the optically active modification may be prepared by way of direct synthesis, e.g. via an optically active compound of the formula VI as described above.

In the method of the present invention the compounds of the formula I will normally be administered orally, rectally or by injection, in the form of pharmaceutical preparations comprising the active ingredient either as a free base or as a pharmaceutically acceptable non-toxic, acid addition salt, e.g. the hydrochloride, hydrobromide, lactate, acetate, phosphate, sulphate, sulphamate, citrate, tartrate, oxalate and the like in association with a pharmaceutically acceptable carrier. Accordingly, terms relating to the compounds of the formula I whether generically or specifically are intended to include both the free amine base and the acid addition salts of the free base, unless the context in which such terms are used, e.g. in the specific examples would be inconsistent with the broad concept. The carrier may be a solid, semisolid or liquid diluent or capsule. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical preparations containing a compound of the formula I in the form of dosage units for oral application the selected compound may be mixed with a solid pulverulent carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol waxes, and the like, and then compressed to form tablets. If coated tablets are required, the cores, prepared as described above, may be coated with a concentration sugar solution which may contain, e.g. gum arabic, gelatine, talcum, titanium dioxide, and the like. Alternatively, the tablet can be coated with a laquer dissolved in a readily volatile organic solvent or mixture of organic solvents. Dyestuffs may be added to these coatings in order to readily distinguish between tablets containing different active substances or different amounts of the active compounds.

For the preparation of soft gelatine capsules (pearl-shaped closed capsules) consisting of gelatine and for example, glycerol or similar closed capsules, the active substance may be admixed with a vegetable oil. Hard gelatin capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example, solutions containing from about 0.2% to about 20% by weight of the active substance herein described, the balance being sugar and a mixture of ethanol, water, glycerol, and propyleneglycol. Optionally such liquid preparations may contain colouring agents, flavouring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

Suitable daily doses of the compounds of the invention in therapeutical treatment of humans are 100 to 500 mg at peroral administration and 20 to 100 mg at parenteral administration.

The preferred method of the invention comprises administration of the compound of the formula

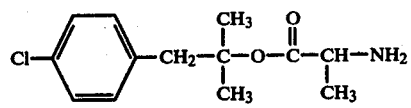

(GEA 654)

Preferably this compound is prepared and used in the form of its hydrochloride monohydrate salt.

The following example illustrates the preparation of pharmaceutical compositions to be used in the method of the invention. For the preparation of tablets the following compositions were made.

| | |
|---|---|
| (a) 2-Aminopropanoic acid 1-(4-chlorophenyl)-2-methyl-2-propylester hydrochloride (GEA 654) | 50 g |
| Lactose | 85 g |
| Potatoe starch | 40 g |
| Polyvinylpyrrolidone | 5 g |
| Cellulose Avicel | 18 g |
| Magnesium stearate | 2 g |
| (b) 2-Aminopropanoic acid 1-(4-chlorophenyl)-2-methyl-2-propylester hydrochloride (GEA 654) | 100 g |
| Lactose | 90 g |
| Potatoe starch | 50 g |
| Polyvinylpyrrolidone | 5 g |
| Cellulose Avicel | 23 g |
| Magnesium stearate | 2 g |

From the above compositions 1000 tablets were made, containing 50 mg and 100 mg of active substance, respectively. If desired, the obtained tablets can be film coated with e.g. methyl cellulose in an organic solvent.

The regional specificity of the inhibition of the 5-HT was determined by studying whether GEA 654, alaproclate (2-(4-chloro-phenyl)-1,1-dimethylethyl-2-aminopropanoate), given i.p. to rats 30 min before H 75/12 ($\alpha$-ethyl-4-methyl-m-tyramine) could prevent the brain 5-HT depletion induced by H 75/12, 50 mg/kg i.p., 2 h before sacrifice. The following results were obtained:

TABLE I

| Dose of alaproclate hydrochloride monohydrate mg/kg i.p. | % Inhibition of 5-HT uptake in | | | | |
|---|---|---|---|---|---|
| | Cortex | Spinal cord | Striatum | Hypothalamus | Hippocampus |
| 1,5 | — | — | — | 10 | 10 |
| 3 | — | 17 | 6 | 25 | 40 |
| 10 | 13 | 33 | 46 | 55 | 74 |

This shows that alaproclate (GEA 654) is most potent in the hippocampus followed by the hypothalamus in the clinically relevant dose level of 3 mg/kg.

The potentiation of the cholinergic response can be derived from tests showing that alaproclate potentiates the oxotremorine induced tremor as well as the psysostigmine induced tremor in mice. Alaproclate was injected i.p. to adult mice 30 min prior to injection s.c. into the neck of the threshold dose for inducing tremor of oxotremorine (semi-bis-fumarate), 100 $\mu$g/kg, or of physostigmine, 200 $\mu$g/kg. Saline was administered as a blank. The tremor intensity was assessed visually for a 60 min period starting from the injection of oxotremorine and physostigmine respectively. The following rating scores were used:

0—no apparent tremor

1—moderate or discontinuous tremor of the head and forelimbs

2—strong tremor involving the whole body

The average score for a given time period and dose of alaproclate was calculated from 6 animals. The results are given in the following Tables 2 and 3.

TABLE 2

Potentiation of oxotremorine induced tremor by alaproclate

| Time after adm. of oxotremorine 100 μg/kg, min. | Mean tremor score after pretreatment with: | | | |
|---|---|---|---|---|
| | Saline | Alaproclate, mg/kg | | |
| | | 20 | 40 | 60 |
| 5 | — | — | 0,3 | 0,1 |
| 10 | 0,3 | 0,7 | 1,0 | 1,0 |
| 15 | 0,3 | 1,0 | 1,3 | 1,5 |
| 30 | 0,2 | 0,8 | 1,2 | 1,6 |
| 60 | — | — | 0,5 | 1,0 |

TABLE 3

Potentiation of physostigmine induced tremor by alaproclate

| Time after adm. of physostigmine 200 μg/kg, min | Mean tremor score after pretreatment with: | | | |
|---|---|---|---|---|
| | Saline | Alaproclate, mg/kg | | |
| | | 20 | 40 | 60 |
| 5 | — | 0,3 | 0,3 | 0,7 |
| 10 | 0,2 | 0,8 | 1,0 | 1,3 |
| 15 | 0,3 | 0,8 | 0,7 | 0,8 |
| 30 | — | — | 0,3 | 0,7 |
| 60 | — | — | — | — |

These values show that alaproclate is able to enhance the oxotremorine induced tremor as well as the physostigmine induced tremor, although alaproclate per se does not cause tremor.

We claim:

1. A method for treatment of senile dementia comprising administration to a patient suffering therefrom an amount of a compound of the formula

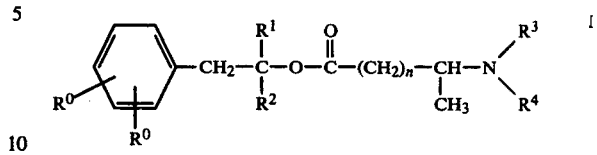

and pharmaceutically acceptable salts thereof, in which formula the groups $R^0$ are the same or different and are selected from the group consisting of hydrogen, halogen, alkyl having 1, 2 or 3 carbon atoms, and alkoxy having 1, 2 or 3 carbon atoms; $R^1$ is hydrogen, methyl or ethyl; $R^2$ is methyl or ethyl; $R^3$ and $R^4$ are the same or different and are hydrogen or an alkyl group having 1, 2 or 3 carbon atoms; and n is 0, 1 or 2, effective to mitigate the symptoms of senile dementia.

2. A method according to claim 1, wherein the compound of the formula I is

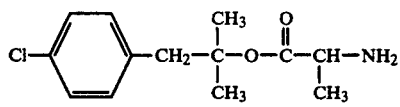

or a pharmaceutically acceptable acid addition salt thereof.

* * * * *

UNITED STATES PATENT AND TRADEMARK OFFICE
CERTIFICATE OF CORRECTION

PATENT NO. : 4,469,707

DATED : September 4, 1984

INVENTOR(S) : Ulf H.A. Lindberg et al

It is certified that error appears in the above-identified patent and that said Letters Patent is hereby corrected as shown below:

Page 1, column 1, item [73], correct "Astra Lakemadel" to

--Astra Lakemedel--;

Column 2, line 4, after "halogen" insert --,--.

Signed and Sealed this

Ninth Day of April 1985

[SEAL]

Attest:

DONALD J. QUIGG

Attesting Officer

Acting Commissioner of Patents and Trademarks